United States Patent
Anklekar et al.

(10) Patent No.: US 10,106,562 B2
(45) Date of Patent: Oct. 23, 2018

(54) PROCESS FOR MANUFACTURE OF GADOFOSVESET TRISODIUM MONOHYDRATE

(71) Applicant: Lantheus Medical Imaging, Inc., North Billerica, MA (US)

(72) Inventors: Tarakeshwar Anklekar, Billerica, MN (US); Jan Haller, Leverkusen (DE); Nicolas Champion, Chuzelles (FR); Franz-Willi Herkenrath, Hennef (DE)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

(21) Appl. No.: 14/774,944

(22) PCT Filed: Mar. 13, 2014

(86) PCT No.: PCT/US2014/025687
§ 371 (c)(1),
(2) Date: Sep. 11, 2015

(87) PCT Pub. No.: WO2014/160039
PCT Pub. Date: Oct. 2, 2014

(65) Prior Publication Data
US 2016/0016979 A1    Jan. 21, 2016

Related U.S. Application Data

(60) Provisional application No. 61/780,132, filed on Mar. 13, 2013.

(51) Int. Cl.
| | | |
|---|---|---|
| C07F 9/117 | (2006.01) | |
| C07F 9/6506 | (2006.01) | |
| C07F 9/146 | (2006.01) | |
| A61K 49/10 | (2006.01) | |
| A61K 31/685 | (2006.01) | |
| A61K 49/04 | (2006.01) | |

(52) U.S. Cl.
CPC ............ *C07F 9/117* (2013.01); *A61K 31/685* (2013.01); *A61K 49/04* (2013.01); *A61K 49/106* (2013.01); *C07F 9/146* (2013.01); *C07F 9/65061* (2013.01)

(58) Field of Classification Search
None
See application file for complete search history.

(56) References Cited

U.S. PATENT DOCUMENTS

| | | | | | |
|---|---|---|---|---|---|
| 5,583,235 | A | * | 12/1996 | Bierer | C07D 231/12 549/20 |
| 5,919,967 | A | * | 7/1999 | Amedio | C07F 9/09 536/25.34 |
| 6,099,824 | A | * | 8/2000 | Anelli | A61K 49/06 424/9.364 |
| 6,121,488 | A | * | 9/2000 | Nikam | C07C 231/02 506/27 |
| 6,559,330 | B1 | * | 5/2003 | Platzek | A61K 49/085 424/9.3 |
| 6,676,929 | B2 | | 1/2004 | McMurry et al. | |
| 2004/0167330 | A1 | * | 8/2004 | Lukes | A61K 49/085 540/474 |
| 2007/0179321 | A1 | * | 8/2007 | Koerner | C07C 29/145 568/17 |
| 2009/0076571 | A1 | * | 3/2009 | Lu | A61K 47/48315 607/88 |
| 2009/0208421 | A1 | * | 8/2009 | Meyer | A61K 49/106 424/9.361 |
| 2010/0094028 | A1 | * | 4/2010 | Lemaire | C07D 493/04 549/464 |
| 2011/0065959 | A1 | | 3/2011 | Bailey et al. | |

FOREIGN PATENT DOCUMENTS

| | | |
|---|---|---|
| CN | 1373765 | 10/2002 |
| CN | 101790410 | 7/2010 |
| WO | WO 1996/023526 | 8/1996 |
| WO | WO 1999/017809 | 4/1999 |
| WO | WO 2001/018011 | 3/2001 |
| WO | WO 0127628 A1 * | 4/2001 ............... C07K 7/62 |

OTHER PUBLICATIONS

EMEA Directive, "EPAR_Scientific_Discussion", EMEA, 2005, pp. 1-33.*
Amedio, J.C., et al., "A practical Manufacturing Synthesis of 1®-hydroxymethyl-DTPA: An important intermediate in the synthesis of MRI contrast agents", Synthetic Communications, 1999, pp. 2377-2391.*
Koszel, D., et al., "The synthesis and biological activity of lipophilic derivatives of bicine conjugated with N3-(4-methoxyfumaroyl)-L-2,3-diaminopropanoic acid (FMDP)—an inhibitor of glucosamine-6-phosphate synthase", J. Enz. Inh. Med. Chem., 2012, pp. 167-173.*
Chen et al., Gadolinium Isotope Separation by Cation Exchange Chromatography, Journal of Nuclear Science and Technology, Nov. 1992, 1086-1092.
Chinese Office Action in Chinese Application No. 201480027015.5, dated Nov. 22, 2016, 14 pages.
Chinese Search Report in Chinese Application No. 201480027015.5, dated Mar. 13, 2013, 5 pages.
Extended European Search Report in European Application No. 14776124.1, dated Sep. 27, 2016, 5 pages.
International Search Report and Written Opinion in International Application No. PCT/US2014/025687, dated Jul. 31, 2014, 17 pages.

(Continued)

*Primary Examiner* — Michael G Hartley
*Assistant Examiner* — Lance W Rider
(74) *Attorney, Agent, or Firm* — Fish & Richardson P.C.

(57) ABSTRACT

This application relates to a process for making a pharmaceutically acceptable formulation of gadofosveset trisodium monohydrate, wherein the process uses no more than one chromatographic purification for removal of impurities.

16 Claims, No Drawings

(56) References Cited

OTHER PUBLICATIONS

McMurry et al., "The effect of a phosphodiester linking group on albumin binding, blood half-line, and relaxivity of intravascular diethylenetriaminepentaacetato aquo gadolinium(III) MRI contrast agents," J. Med. Chem., 2002, 45: 3465-3474.
Singapore Search Report and Written Opinion in Singapore Application No. 11201507458U, dated Aug. 16, 2016, 10 pages.

* cited by examiner

PROCESS FOR MANUFACTURE OF GADOFOSVESET TRISODIUM MONOHYDRATE

CROSS REFERENCE TO RELATED APPLICATIONS

This application is a § 371 National Stage application of International Application No. PCT/US2014/025687, filed Mar. 13, 2014, which claims the benefit of U.S. Provisional Ser. No. 61/780,132 filed Mar. 13, 2013, each of which is incorporated herein by reference in its entirety.

TECHNICAL FIELD

This application relates to processes for making a pharmaceutically acceptable formulation of gadofosveset trisodium monohydrate.

BACKGROUND

Gadolinium-based contrast agents are used to improve visibility of internal structures when a patient undergoes a magnetic resonance imaging (MRI) procedure. These agents are typically administered intravenously immediately prior to imaging. One important contrast agent is gadofosveset trisodium monohydrate (Ablavar®) (structure shown below).

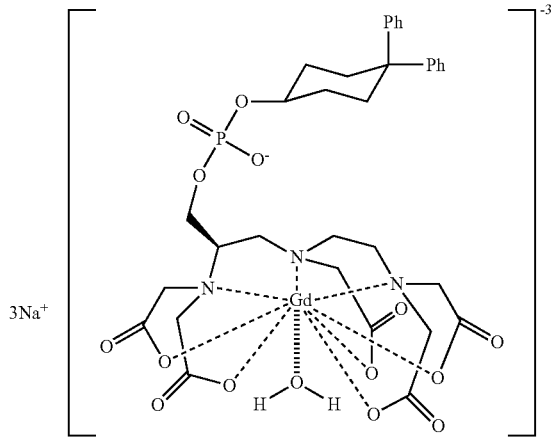

Because gadofosveset trisodium monohydrate is administered intravenously, it is important to provide the agent in a pharmaceutically acceptable formulation. Further, there is a need to reduce the number of chromatographic steps used to obtain pharmaceutically acceptable purity for the contrast agent, as additional steps can reduce yields and increase cost. This application addresses these needs and others.

SUMMARY

The present application provides a process for preparing a pharmaceutically acceptable formulation of gadofosveset trisodium monohydrate. The process unexpectedly allows for the formation of a pharmaceutically acceptable formulation of gadofosveset trisodium monohydrate having low impurities without requiring the use of multiple chromatographic separations, which can reduce yield.

The details of one or more embodiments of the invention are set forth in the accompanying drawings and the description below. Other features, objects, and advantages of the invention will be apparent from the description and drawings, and from the claims.

DETAILED DESCRIPTION

The present application provides a process for preparing a pharmaceutically acceptable formulation of gadofosveset trisodium monohydrate, optionally comprising no more than one chromatographic purification, for the removal of impurities. In some embodiments, the formulation comprises equal to or less than 0.5% total impurities based on gadofosveset trisodium monohydrate. In some embodiments, the formulation comprises equal to or less than 0.7%, 0.67%, 0.6%, 0.5%, 0.4%, 0.3%, 0.2%, 0.1%, 0.09%, 0.08%, 0.07%, 0.06%, or 0.05% total impurities based on gadofosveset trisodium monohydrate. Impurities can be measured by various techniques know in the art, including, but not limited to HPLC (High Performance Liquid Chromatography).

As used herein, chromatographic purification refers to the use of a chromatographic device or method for separating mixtures which are dissolved in a mobile phase. Example separation methods include HPLC, SFC (Supercritical Fluid Chromatography), both in batch mode and in continuous mode, e.g., SMB (Simulated Moving Bed), and related techniques. Such methods include, but are not limited to, traditional single column batch chromatography, continuous chromatography, or a steady state, sequential injection processes. Continuous chromatographic methods include, but are not limited to multicolumn continuous chromatographic processes, including such countercurrent chromatographic processes as SMB or a non-steady state continuous chromatographic method known as the "Varicol™" Process. Chromatographic processes as described herein do not include simple filtration techniques such as ion-exchange or bulk clean-up procedures such as filtration through short silica columns, commonly known in the art as plug filtration.

The present application further provides a process for preparing a pharmaceutically acceptable formulation of gadofosveset trisodium monohydrate, comprising:

(a) reacting 4,4-diphenylcyclohexanol with phosphorus trichloride to form dichloro((4,4-diphenylcyclohexyl)oxy)phosphine;

(b) reacting dichloro((4,4-diphenylcyclohexyl)oxy)phosphine with 1H-imidazole to form 1,1'-(((4,4-diphenylcyclohexyl)oxy)phosphinediyl)bis(1H-imidazole);

(c) reacting 1,1'-(((4,4-diphenylcyclohexyl)oxy)phosphinediyl)bis(1H-imidazole) with a compound of Formula (1):

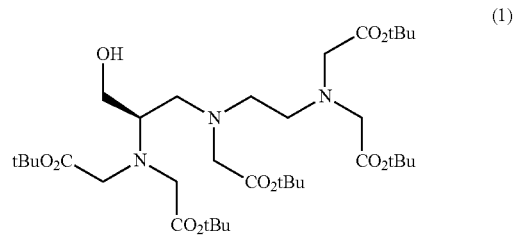 [SMILES: CC(C)(C)OC(=O)CN(CCN(CC(=O)OC(C)(C)C)C[C@H](CO)N(CC(=O)OC(C)(C)C)CC(=O)OC(C)(C)C)CC(=O)OC(C)(C)C]

to form a compound of Formula (2):

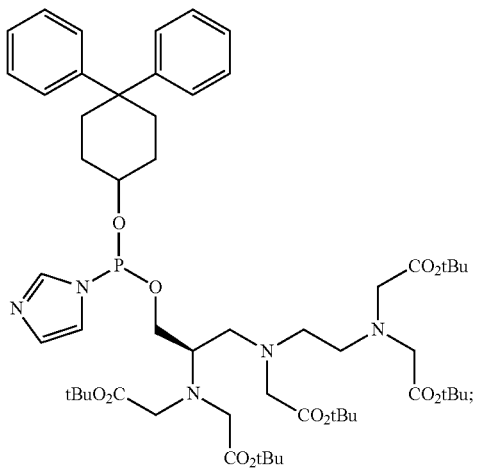

(d) hydrolyzing and oxidizing the compound of Formula (2) in the presence of hydrochloric acid and hydrogen peroxide to form a compound of Formula (3):

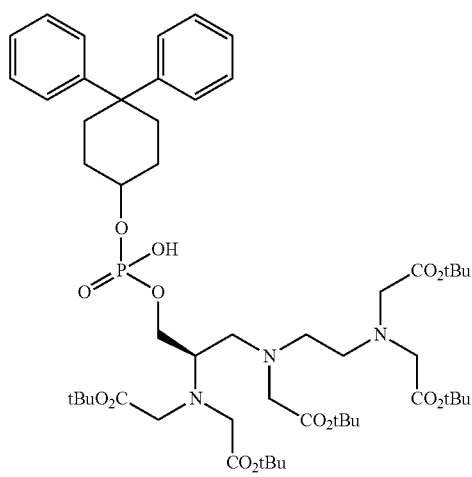

followed by further hydrolysis in the presence of hydrochloric acid to form fosvoset;

(e) reacting an aqueous solution of fosveset with gadolinium oxide, followed by reaction with sodium hydroxide to form gadofosveset trisodium monohydrate;

wherein said process preferably comprises no more than one chromatographic purification for removal of impurities.

Synthetic processes which reduce the number of chromatographic purification steps are preferred during the bulk manufacture of pharmaceuticals. As is known in the art, the term bulk manufacture refers to the large scale production of material required to support the commercial sale and use of pharmaceuticals. The practice of bulk manufacture is readily distinguished from the smaller, laboratory scale processes used for non-commercial purposes. One of ordinary skill will appreciate that processes for large scale removal of impurities are constrained by the high material cost and limited availability of suitable chromatographic equipment.

In some embodiments, the processes described herein are performed at a scale of about 10 kg to about 70 kg, about 20 kg to about 60 kg, about 30 kg to about 60 kg, about 40 kg to about 60 kg, or about 50 kg to about 60 kg.

In some embodiments, the reacting of 4,4-diphenylcyclohexanol with phosphorus trichloride is carried out at a temperature of about −20° C. to about −10° C., or at a temperature of about −12° C. to about −20° C. in a solvent comprising tetrahydrofuran. In some embodiments, about 1 to about 1.2 equivalents of phosphorus trichloride are used per equivalent of 4,4-diphenylcyclohexanol in (a). In some embodiments, from about 1.1 to 1.15 equivalents of phosphorus trichloride are used per equivalent of 4,4-diphenylcyclohexanol in (a). In some embodiments, the product from (a) is used without isolation or purification in the reaction of (b).

In some embodiments, the reacting of the dichloro((4,4-diphenylcyclohexyl)oxy)phosphine with 1H-imidazole is carried out by a process comprising adding a solution of 1H-imidazole in tetrahydrofuran to the solution of dichloro ((4,4-diphenylcyclohexyl)oxy)phosphine in tetrahydrofuran at a temperature of about 0° C. to about 15° C. and stirring the solution for about one hour at about 10° C. to about 20° C., or at about 12° C. to about 18° C. In some embodiments, about 4 to about 6 equivalents, about 4.5 to about 5 equivalents, or about 4.7 to 5 equivalents of 1H-imidazole are used per equivalent of dichloro((4,4-diphenylcyclohexyl)oxy) phosphine. In some embodiments, the product from (b) is used without isolation or purification in the reaction of (c).

In some embodiments, the reacting 1,1'-(((4,4-diphenyl-cyclohexyl)oxy)phosphinediyl)bis(1H-imidazole) with a compound of Formula (1) is carried out by a process comprising adding a heptane solution of the compound of Formula (1) to a tetrahydrofuran solution of 1,1'-(((4,4-diphenylcyclohexyl)oxy)phosphinediyl)bis(1H-imidazole) from (b) at about 10° C. to about 20° C., or at about 12° C. to about 18° C., and stirring the solution for about one hour. In some embodiments, the product from (c) is used without isolation or purification in the reaction of (d).

In some embodiments, the hydrolyzing and oxidizing of the compound of Formula (2) is carried out by a process comprising adding water and adjusting the pH of 2.5 to 3 with hydrochloric acid at about 10° C. to about 20° C., or at about 12° C. to about 18° C., and then adding hydrogen peroxide and stirring for about 15 to about 20 hours, or about 15 hours. In some embodiments, the hydrolysis of the compound of Formula (3) is carried out in the presence of water and hydrochloric acid. In some embodiments, fosvoset from (d) is isolated by a process comprising separating the aqueous phase and treating said aqueous phase with sodium hydroxide to a pH of about 2.5 to about 3.5, followed by extraction with tetrahydrofuran, followed by a second treatment with sodium hydroxide to adjust the pH to about 5.5 to about 6.5, followed by distillation to remove tert-butanol and solvent, followed by addition of water and hydrochloric acid to a pH of 1.5 to about 2, followed by collection by filtration.

In some embodiments, the reacting of the aqueous solution of fosveset with gadolinium oxide is carried out by a process comprising adjusting the pH of the aqueous solution of fosveset at a pH of less than about 5, to about 3.5 to about 4, or about 3.7, with hydrochloric acid and treating with at least one equivalent, or about 1 to about 1.01 equivalent, of gadolinium oxide at about 50° C. to about 65° C., or about 55° C. to about 60° C., followed by heating to about 85° C. to about 95° C. In some embodiments, the process further comprises adjusting the pH of the solution to about 5.5 to about 6 with sodium hydroxide and heating at about 85° C. to about 95° C. to form gadofosveset trisodium monohydrate.

In some embodiments, the process further comprises filtering an aqueous solution of gadofosveset trisodium monohydrate at a pH greater than 7.5. This step allows the removal of excess gadolinium. In some embodiments, the solution is filtered at a pH of about 9 to about 12, or about 10.5.

In some embodiments, the process comprises treating an aqueous solution of gadofosveset trisodium monohydrate with a strong acid cation resin. This step allows the removal of excess gadolinium. In some embodiments, the pH of the solution is about 6 to about 7, or about 6.5. In some embodiments, the strong acid cation resin comprises polystyrene crosslinked by divinylbenzene (e.g., Applexion XA 2033, from Novasep).

In some embodiments, the process further comprises adjusting the pH of the aqueous solution of gadofosveset trisodium monohydrate after the treating to a pH of about 6 to about 7, about 6.2 to about 6.8, or about 6.5, with hydrochloric acid, followed by ultrafiltration to remove endotoxin, concentrating by nanofiltration, and spray drying to form gadofosveset trisodium monohydrate.

In some embodiments, the process comprises, prior to (c):

(i) reacting (R)-2-amino-3-((2-aminoethyl)amino)propan-1-ol trihydrochloride with tert-butyl 2-bromoacetate in the presence of a diisopropylethylamine and potassium iodide in a solvent comprising dimethylformamide to form a solution comprising a compound of Formula (1);

(ii) after (i), treating the solution with diethanolamine at about 40° C. to about 60° C.;

(iii) after (ii), adding the solution to a mixture of water and heptane, separating the organic phase, and extracting the organic phase with water to form an organic solution of the compound of Formula (1); and (iv) after (iii), filtering the organic solution through a short column of silica gel.

In some embodiments 5 to 6 equivalents of tert-butyl 2-bromoacetate are used per equivalent of (R)-2-amino-3-((2-aminoethyl)amino)propan-1-ol. In some embodiments, the reacting of (R)-2-amino-3-((2-aminoethyl)amino)propan-1-ol trihydrochloride is conducted with 5 to 6 equivalents of tert-butyl 2-bromoacetate in the presence of a diisopropylethylamine and potassium iodide in dimethylformamide to form a solution of a compound of Formula (1). In some embodiments, about 5.5 equivalents of tert-butyl 2-bromoacetate are used per equivalent of (R)-2-amino-3-(2-aminoethyl)amino)propan-1-ol. In some embodiments, about 3 to about 4 equivalents, or about 3 to about 3.5 equivalents, of potassium iodide are used per equivalent of (R)-2-amino-3-((2-aminoethyl)amino)propan-1-ol. In some embodiments, about 8 to about 9 equivalents, or about 8.4 to about 8.6 equivalents, of diisopropylethylamine are used per equivalent of (R)-2-amino-3-((2-aminoethyl)amino)propan-1-ol. In some embodiments, the reacting in (i) is carried about by adding potassium iodide to a tetrahydrofuran solution of (R)-2-amino-3-((2-aminoethyl)amino)propan-1-ol at about 20° C. to about 30° C., or at about 22° C. to about 28° C., followed by cooling to about 5° C. to about 15° C., or at about 7° C. to about 13° C., adding the diisopropylethylamine, adding the tert-butyl 2-bromoacetate, and then stirring at about 45° C. to about 55° C., or about 47° C. to about 53° C.

In some embodiments, (ii) is carried about at a temperature of about 45° C. to about 55° C., or about 47° C. to about 53° C. In some embodiments about 0.9 to about 1.1 equivalents, about 0.95 to about 1.05 equivalents of diethanolamine per equivalent of (R)-2-amino-3-((2-aminoethyl)amino)propan-1-ol. Diethanolamine is used to consume excess tert-butyl 2-bromoacetate, which improves purity of the heptane solution of the compound of Formula (1).

In some embodiments, said filtering the organic solution is performed using a short column of silica gel in heptane.

In some embodiments, the process further comprises, prior to (c):

(i-a) reacting L-serine methyl ester hydrochloride with di-tert-butyl dicarbonate in the presence of triethylamine in a solvent comprising toluene to form N-(tert-butoxycarbonyl)-L-serine methylester;

(i-b) after (i-a), washing the solution with an aqueous brine solution;

(i-c) after (i-b), reacting the N-(tert-butoxycarbonyl)-L-serine methylester in toluene with 1,2-ethylenediamine to form a solution of (S)-tert-butyl (1-((2-aminoethyl)amino)-3-hydroxy-1-oxopropan-2-yl)carbamate in toluene;

(i-d) after (i-c), concentrating the solution to form a solid, slurrying the solid, concentrating the slurry to form a solid, and crystallizing the solid from a solvent comprising tetrahydrofuran;

(i-e) after (i-d), reacting (S)-tert-butyl (1-((2-aminoethyl)amino)-3-hydroxy-1-oxopropan-2-yl)carbamate with diborane produced in situ to form (R)-tert-butyl (1-((2-aminoethyl)amino)-3-hydroxypropan-2-yl)carbamate; and (i-f) after (i-e), reacting (R)-tert-butyl (1-((2-aminoethyl)amino)-3-hydroxypropan-2-yl)carbamate with hydrochloric acid in water to form (R)-2-amino-3-((2-aminoethyl)amino)propan-1-ol trihydrochloride.

In some embodiments, in (i-a), the reacting L-serine methyl ester hydrochloride with di-tert-butyl dicarbonate is carried out by a process comprising adding triethylamine to a mixture of L-serine methyl ester hydrochloride and di-tert-butyl dicarbonate at about 10° C. to about 20° C., or about 12° C. to about 18° C., followed by warming the solution to ambient temperature. In some embodiments, about 1 to about 1.05 equivalents, or about 1 to about 1.01 equivalents of di-tert-butyl dicarbonate are used per equivalent of L-serine methyl ester hydrochloride. In some embodiments, about 1 to about 1.2 equivalents, or about 1.1 to about 1.15 equivalents of triethylamine are used per equivalent of L-serine methyl ester hydrochloride.

In some embodiments, a 10% aqueous brine solution is used in (i-b). In some embodiments, about 0.7 to about 0.8 liters, or about 0.75 liters, of 10% brine solution are used per liter of toluene solution of N-(tert-butoxycarbonyl)-L-serine methylester from (i-a). In some embodiments, the concentration of N-(tert-butoxycarbonyl)-L-serine methylester in toluene before addition of the brine solution is about 1.5 M to about 1.7 M, or about 1.6 M to about 1.65 M.

In some embodiments, after separating the organic phase after washing with brine, the reacting of the N-(tert-butoxycarbonyl)-L-serine methylester with 1,2-ethylenediamine is carried out in toluene at a temperature of 20° C. to about 30° C., or about 20° C. to about 26° C. in toluene. In some embodiments, about 6 to about 6.5 equivalents, or about 6 to about 6.1 equivalents of 1,2-ethylenediamine are used per equivalent of N-(tert-butoxycarbonyl)-L-serine methylester.

In some embodiments, the reacting of (S)-tert-butyl (1-((2-aminoethyl)amino)-3-hydroxy-1-oxopropan-2-yl)carbamate with diborane gas is carried about by a process comprising bubbling the diborane gas through a solution of (S)-tert-butyl (1-((2-aminoethyl)amino)-3-hydroxy-1-oxopropan-2-yl)carbamate in tetrahydrofuran at a temperature of about −5° C. to about 5° C., or about −3° C. to about 3° C. and then warming to ambient temperature. In some embodiments, the reacting of (R)-tert-butyl (1-((2-aminoethyl)amino)-3-hydroxypropan-2-yl)carbamate with hydrochloric acid is carried out by a process comprising treating the tetrahydrofuran solution from (i-e) with dilute hydrochloric acid solution, removing the organic solvent by distillation, cooling to about 10° C. to about 25° C., filtering to remove boric acid, further concentrating the solution, and filtering to remove boric acid.

In some embodiments, in (i-f), the hydrochloric acid is concentrated hydrochloric acid. In some embodiments, in (i-f), the reacting of (R)-2-amino-3-((2-aminoethyl)amino)propan-1-ol with hydrochloric acid is carried out by a process comprising adding concentrated hydrochloric acid to precipitate the solid; and collecting the solid by filtration.

In some embodiments, the process comprises prior to step (a), hydrogenating 4,4-diphenylcyclohex-2-enone in tetrahydrofuran in the presence of Raney nickel and hydrogen. In some embodiments, about 0.2 to about 0.4 equivalents, about 0.25 to about 0.35 equivalents, or about 0.25 to about 0.3 equivalents, of Raney nickel is used per equivalent of 4,4-diphenylcyclohex-2-enone.

As used herein, "tBu" is tert-butyl.

Methods of Use and Compositions

In some embodiments, the present application provides a method for magnetic resonance imaging of a biological component comprising administering to a patient a diagnostically effective amount of gadofosveset trisodium monohydrate prepared according to any one of the processes described herein, and forming an image therefrom.

In some embodiments, the present application provides methods for x-ray imaging of a biological component comprising administering to a patient a diagnostically effective amount of gadofosveset trisodium monohydrate prepared according to any one of the processes described herein, and forming an image therefrom.

In another embodiment, the present application provides a pharmaceutically acceptable formulation of gadofosveset trisodium monohydrate prepared according to any one of the processes described herein.

In another embodiment, the present application provides method of administering gadofosveset trisodium monohydrate prepared according to any of the processes described herein, comprising the steps of:

a) withdrawing a patient's blood into a syringe that contains said gadofosveset trisodium monohydrate;

b) mixing the blood and said gadofosveset trisodium monohydrate in the syringe; and c) reinjecting the mixture into the patient.

As used herein, the term "patient," used interchangeably, refers to any animal, including mammals, preferably mice, rats, other rodents, rabbits, dogs, cats, swine, cattle, sheep, horses, or primates, and most preferably humans.

For injection, the formulated agents should have only moderate viscosity to allow for rapid, convenient injections. The viscosity should be less than 10 centipoise, or preferably less than 5 centipoise, or more preferably less than 2 centipoise. For injection, the formulated agents should also not have excessive osmolality, since this can increase toxicity. The osmolality should be less than 3000 milliosmol/kg, or preferably less than 2500 milliosmol/kg, or most preferably less than 900 milliosmol/kg.

The pharmaceutical compositions of this invention comprise gadofosveset trisodium monohydrate prepared according to any one of the processes described herein together with any pharmaceutically acceptable carrier, adjuvant or vehicle. Pharmaceutically acceptable carriers, adjuvants and vehicles that may be used in the pharmaceutical compositions include, but are not limited to, ion exchangers, alumina, aluminum stearate, lecithin, serum proteins, such as human serum albumin, buffer substances such as phosphates, glycine, sorbic acid, potassium sorbate, TRIS (tris(hydroxymethyl)aminomethane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropyleneblock polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long chain alcohol diluent or dispersant, such as Ph. Helv. or similar alcohol. It may be desirable to inject the agent pre-bound to a sterile albumin or plasma replacement solution. Alternatively, an apparatus/syringe can be used that contains the contrast agent and mixes it with blood drawn up into the syringe; this is then re-injected into the patient.

The pharmaceutical compositions comprising gadofosveset trisodium monohydrate may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intrasynovial, intrasternal, intrathecal, intrahepatic, intralesional and intracranial injection or infusion techniques.

When administered orally, the pharmaceutical compositions may be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions may be prepared by mixing the agent with a suitable nonirritating excipient which is solid at ambient temperature but liquid at rectal temperature and therefore will melt in the rectum to release the drug. Such materials include cocoa butter, beeswax and polyethylene glycols.

As noted before, the pharmaceutical compositions of this invention may also be administered topically, especially when the target of treatment includes areas or organs readily accessible by topical application, including the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this invention are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage depends on the sensitivity of the diagnostic imaging instrumentation, as well as the composition of the contrast agent. For example, for MRI imaging, a contrast agent containing a highly paramagnetic substance, e.g., gadolinium (III), generally requires a lower dosage than a contrast agent containing a paramagnetic substance with a lower magnetic moment, e.g., iron (III). Preferably, dosage will be in the range of about 0.001 to 1 mmol/kg body weight per day of the active metal-ligand complex. More preferably, dosage will be in the range of about 0.005 and about 0.05 mmol/kg body weight per day.

It should be understood, however, that a specific dosage regimen for any particular patient will also depend upon a variety of factors, including the age, body weight, general health, sex, diet, time of administration, rate of excretion, drug combination, and the judgment of the treating physician.

Following administration of the appropriate dosage of gadofosveset trisodium monohydrate, prepared according to any one of the processes described herein, or composition thereof, magnetic resonance imaging is performed. The choice of pulse sequence (inversion recovery, IR; spin echo, SE, echo planar, EPI; time-of-flight, TOF; turbo-flash; gradient echo, GE) and the values of the imaging parameters (echo time, TE; inversion time, TI; repetition time, TR; flip angel, etc.) will be governed by the diagnostic information sought. In general, if one desires to obtain T1-weighted images, then TE should be less than 30 milliseconds (or the minimum value) to maximize T1-weighting. Conversely, if one desires to measure T2, then TE should be greater than 30 milliseconds to minimize competing T1 effects. TI and TR will remain approximately the same for both T1 and T2-weighted images; TI and TR are generally on the order of about 5-1000 and 2-1000 milliseconds, respectively.

Gadofosveset trisodium monohydrate is useful for general imaging of tumors, blood-brain-barrier breakdown, and other lesions. In addition, it is very useful for examining perfusion, i.e., the blood flow into and out of tissues (heart, brain, legs, lungs, kidneys, tumors, etc.), and blood vessels (MR angiography). In addition, the agents can be used to enhance the signal changes in the brain during cognitive events (functional MRI).

It is contemplated that the gadofosveset trisodium monohydrate may also be used to enhance diagnostic x-ray imaging. In these cases, the doses of the agent will be approximately equal to that in MRI (0.001-10 mmol/kg). For all techniques, the use and administration of contrast agents and the settings on the imaging machines are known in the art or uses commonly accepted principles.

EXAMPLES

Example 1. Preparation of 4,4-diphenylcyclohexanol

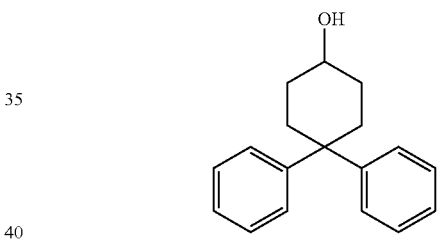

Raney Nickel (67 g, 1.14 mol) was carefully added to a solution of 4,4-diphenylcyclohex-2-enone (1 kg, 4.03 mol) in tetrahydrofuran (3 L) at −3° C. to 3° C. under nitrogen, using a small amount of tetrahydrofuran as a rinse. The reaction vessel was purged with nitrogen, allowed to warm to ambient temperature and pressurized with hydrogen at 5 bar. An exotherm causes the temperature to rise to about 30° C., and the reaction mixture was then stirred until the pressure stabilized. The hydrogen headspace was replaced with nitrogen, and the mixture stirred 1 h at 40° C. The warm solution was filtered, and the filter cake was washed with tetrahydrofuran (500 mL), followed by distilled water (250 mL). The solution was concentrated by distillation, not allowing the temperature to exceed 82° C. Methanol (4 L) was added, and the distillation continued until about half the volume remained. The solution was cooled to −3° C. to 3° C., the product isolated, washed with cold methanol then dried in vacuo at 50° C. to yield the title compound (925 g). The mother liquor from the first crop was concentrated to approximately 30% of the original volume, and a second crop of the title compound was isolated (51 g).

Example 2. Preparation of (S)-tert-butyl (1-((2-aminoethyl)amino)-3-hydroxy-1-oxopropan-2-yl)carbamate

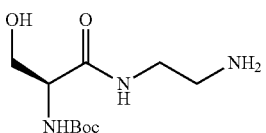 [SMILES: CC(C)(C)OC(=O)N[C@@H](CO)C(=O)NCCN]

A stirred mixture of L-serine methyl ester hydrochloride (1 kg, 6.42 mol) in toluene (4 L) at 12-18° C. was treated with di-tert-butyl dicarbonate (1.42 kg, 6.48 mol), then treated over 1 to 2 h with triethylamine (726 g, 7.17 mol). The reaction was then warmed to ambient temperature and stirred an additional 2 h. The reaction mixture was cooled slightly, treated with 10% brine solution (3 L), stirred briskly for 30 min and let stand 45 min to allow phase separation. The organic phase was separated and added over 1-3 h to a solution of 1,2-ethylendiamine (2.34 kg, 38.9 mol) in toluene (1200 mL) while maintaining the temperature at 20-26° C. The reaction mixture was stirred 5 h at ambient temperature then concentrated at 60° C. under reduced pressure. The product was re-slurried in xylene (5 L) and again concentrated at 60° C. under reduced pressure. The resultant solid was dissolved in tetrahydrofuran (7 L) at 54-60° C., held for one hour at 54-60° C. then allowed to cool to ambient temperature. The resultant solid was isolated by filtration, washed with a small amount of tetrahydrofuran and dried in vacuo to yield the title compound (1.27 kg).

Example 3. Preparation of (R)-2-amino-3-(2-aminoethylamino)-1-propanol, trihydrochloride

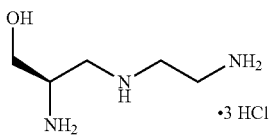

Diborane gas was produced in situ and then bubbled through a solution of the product of Example 2 (1 kg, 4.04 mol) in tetrahydrofuran (9 L) at −3° C. to 3° C. The solution was allowed to warm to ambient temperature, stirred an additional 12 h then re-cooled to −3° C. to 3° C. and treated with dilute aqueous hydrochloric acid (4 L). The reaction vessel was purged with nitrogen then heated to 95-110° C. to remove tetrahydrofuran. The reaction mixture was cooled to 10-25° C., maintained 3 h and filtered to remove boric acid. The filter cake was washed with distilled water, and the filtrate and washes concentrated by distillation at reduced pressure. The distillation pot was cooled to ambient temperature, and a second crop of boric acid removed by filtration. The filter cake was again washed with distilled water, and the filtrate and washes concentrated under reduced pressure. Concentrated hydrochloric acid was then added to the distillation pot at ambient temperature until the hydrochloric acid molarity was greater than 7. A mixture of n-butanol (700 mL) and ethanol (390 mL) was then slowly added to the aqueous reaction mixture at ambient temperature, and stirring continued for at least 3 h. The precipitated product was collected by filtration, successively washed with acidified ethanol and ethanol then dried to yield the title compound (696 g).

Example 4. Preparation of 1-hydroxymethyldiethylenetriaminepentaacetic acid, penta-tert-butyl ester (Formula (1))

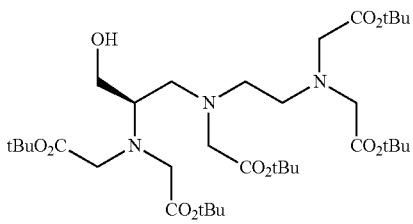 [SMILES: CC(C)(C)OC(=O)CN(CCN(CC(=O)OC(C)(C)C)C[C@H](CO)N(CC(=O)OC(C)(C)C)CC(=O)OC(C)(C)C)CC(=O)OC(C)(C)C]

Potassium iodide (2.1 kg, 12.7 mol) was added portionwise to a stirred solution of the product of Example 3 (1 kg, 4.12 mol) in dimethylformamide (6.7 L) while maintaining the temperature at 22-28° C. The reaction mixture was then stirred 1 h, cooled to 7-13° C., and treated with diisopropylethylamine (4.53 kg, 35.1 mol); additional dimethylformamide (5 L) was used as a rinse. The reaction mixture was stirred at 7-13° C. for 1 h then treated with t-butyl bromoacetate (4.42 kg, 22.7 mol) over a period of 1 h while maintaining the temperature below 50° C.; additional dimethylformamide (16 L) was used as a rinse. The reaction mixture was then stirred at 47-53° C. and monitored by HPLC. Upon completion, a solution of diethanolamine (430 g, 4 mol) in dimethylformamide (450 mL) was added along with dimethylformamide (6.7 L) as a rinse. After 2 h at 47-53° C., the reaction mixture was cooled to 17-23° C. then transferred to a stirred mixture of distilled water (5 L) and heptane (7 L). The reaction vessel was then washed with dimethylformamide (100 mL), and distilled water (5 L), and the combined washes added to the water/heptane mixture. After stirring 30 min at 17-23° C., the reaction mixture was left to stand 45 min to allow for phase separation. The organic phase was then separated, washed twice with distilled water and passed through a short column of silica gel with heptane as the eluent, to provide the title compound as a solution in heptane (assayed as containing 2.3 kg).

Example 5A. Preparation of 2,2'-((2-(((2R)-2-(bis(carboxymethyl)amino)-3-((((4,4-diphenylcyclohexyl)oxy)(hydroxy)phosphoryl)oxy)propyl)(carboxymethyl)amino)-ethyl)azanediyl)diacetic acid (fosveset)

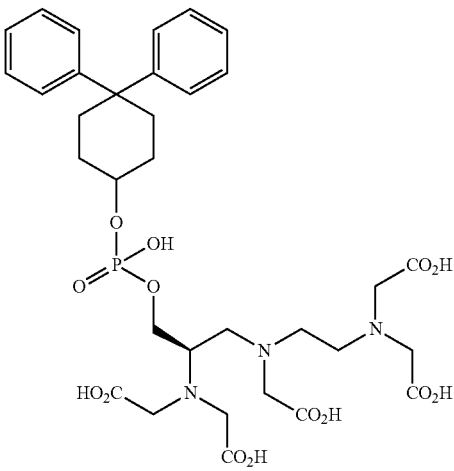 [SMILES: O=C(O)CN(CCN(CC(=O)O)C[C@H](COP(=O)(O)OC1CCC(c2ccccc2)(c2ccccc2)CC1)N(CC(=O)O)CC(=O)O)CC(=O)O]

The product of Example 1 (431 g, 1.7 mol) in dry tetrahydrofuran (24 L) was added over a 10 h period to a solution of phosphorous trichloride (261 g, 1.9 mol) in tetrahydrofuran (11 L) at −18 to −12° C. The reaction mixture was stirred for an additional 2 h at −18 to −12° C., diluted into tetrahydrofuran (22 L), cooled to 0 to 8° C. then treated with a solution of 1H-imidazole (564 g, 8.3 mol) in tetrahydrofuran (22 L) at 0 to 15° C. The reaction mixture was allowed to warm to 12-18° C. then stirred 1 h. A heptane solution of the product of Example 4 was then added over a period of 1 h to the reaction mixture. Stirring was continued for an additional 1 h then distilled water (1.4 L) was added to the reaction vessel, followed by heptane (1.5 L). While continuing to maintain the temperature at 12-18° C., half concentrated hydrochloric acid was added until the pH measured 2.5 to 3.0. The reaction was stirred for 30 min then 35% hydrogen peroxide (166 mL) was added. After stirring 15 h at ambient temperature, the reaction mixture was cooled to 12-18° C., washed three times with sodium metabisulfite solution, once with distilled water then successively treated with concentrated hydrochloric acid (2.8 L) and distilled water (1.8 L). The aqueous phase was separated then treated with 30% aqueous sodium hydroxide solution to adjust the pH to 2.8-3.5; the separated organic phase was collected and discarded. The aqueous phase was then treated with 2.5 L tetrahydrofuran, stirred 30 min, and the phases again allowed to separate. This process was repeated, and the aqueous phase once again separated then treated with 30% aqueous sodium hydroxide solution to adjust the pH to 5.5-6.5. The resulting solution was then heated to 80° C. at 400 mbar to remove tert-butanol and tetrahydrofuran. Upon completion, the distillation pot was cooled to 17-23° C., diluted with 5 L distilled water then treated with half concentrated hydrochloric acid to adjust the pH to 1.5 to 1.8. The solution was again cooled to 0 to 6° C., stirred 3 h, and the resultant solid collected by filtration. Washing with cold acidified water (pH 1.4 to 1.8) and drying provided the title compound (815 g).

Example 5B. Purification of 2,2'-((2-(((2R)-2-(bis(carboxymethyl)amino)-3-((((4,4-diphenylcyclohexyl)oxy)(hydroxy)phosphoryl)oxy)propyl)(carboxymethyl)amino)-ethyl)azanediyl)diacetic acid (fosveset)

A suspension of the stationary phase (77 kg) and isopropyl alcohol (250 L) was prepared in a 1000 L reactor then transferred into the DAC column housing and compressed to a final bed length of 23.6 cm. After equilibration, an aqueous solution of the crude fosveset (~2 kg) was loaded onto the column and the purification performed using water (1 min at 15 L/min and 8.5 min at 30 L/min) and methanol (4 min at 30 L/min). The main product peak eluting between 7 and 11.75 min was collected, pooled and used directly in the gadolinium complexation. A total of 29 discrete injections were required for the purification of ~57 kg of crude material.

Example 6A. Preparation of Gadofosveset Trisodium Monohydrate

A solution of the product from Example 5B (49.1 kg) in water (200 L) was adjusted to a pH of 3.7 using dilute aqueous hydrochloric acid, then heated to 55-60° C., and treated with gadolinium oxide (12.1 kg). The reaction mixture was then warmed to 85-95° C. and maintained 2 h. The pH of the mixture was increased to 5.5-6, using 4% aqueous sodium hydroxide then maintained 1 h at 85-95° C. The mixture was cooled to ambient temperature, and additional 4% aqueous sodium hydroxide was added to raise the solution pH to 6.5. Free (unreacted) gadolinium was then removed by initial filtration through silica, followed by cation exchange with sodium using a strong acid resin (e.g. Applexion XA 2033, Novasep). The pH of the resulting eluate was then adjusted to 6.5 with 33% aqueous hydrochloric acid, ultrafiltered to remove endotoxin then concentrated by nanofiltration, and spray dried to produce the title compound.

Example 6B. Alternative Preparation of Gadofosveset Trisodium Monohydrate

A solution of the product from Example 5B (49.1 kg) in water (200 L) was adjusted to a pH of 3.7 using dilute aqueous hydrochloric acid, then heated to 55-60° C., and treated with gadolinium oxide (12.1 kg). The reaction mixture was then warmed to 85-95° C. and maintained 2 h. The pH of the mixture was increased to 5.5-6, using 4% aqueous sodium hydroxide then maintained 1 h at 85-95° C. The mixture was cooled to ambient temperature, and additional aqueous sodium hydroxide solution added to raise the solution pH to 10.5. Excess gadolinium was then removed by filtration, and the pH of the filtrate adjusted to 6.5 with aqueous hydrochloric acid. The solution was ultrafiltered to remove endotoxin then concentrated by nanofiltration, and spray dried to produce the title compound.

Example 7. Representative Batch Characterization of Gadofosveset Trisodium Monohydrate of the Invention

| Analysis | Specification | Results |
| --- | --- | --- |
| Aspect | White to slightly yellow powder or granular powder | Conform |
| Color at 450 nm (AU) | ≤0.030 AU | 0.012 AU |
| Identification: IR | To Pass Test | Conform |
| Identification: Sodium | To Pass test | Conform |
| MS-32520-R assay (% w/w) | 97.0-103.0% | 99.9% |
| Chloride (as NaCl; % w/w) | ≤2% | <0.02% |
| Heavy metals (% w/w) | ≤0.002% | Conform |
| Soluble silicon (as Si; % w/w) | ≤0.05% | <0.02% |
| Free Gd(III) content (% w/w) | ≤0.02% | <0.016% |
| Gd-EDTA content (% w/w) | ≤0.10% | ND |
| Gd-HMDTPA content (% w/w) | ≤0.10% | <0.025% |
| MS-32516-R assay (% w/w) | ≤0.13% | <0.02% |
| MS-32509 phosphate content (% w/w) | ≤0.05% | ND |
| MS-32516 lactam content (% w/w) | ≤0.12% | <0.02% |
| N-Methyl MS-32520-R | ≤0.07% | <0.02% |
| Overalkylated MS-32516 | ≤0.09% | <0.02% |
| Unspecified impurity (0.6 RRT) | ≤0.11% | ND |
| Unspecified impurity (1.2 RRT) | ≤0.25% | ND |
| Total residual solvent content (% w/w) | ≤0.5% | ND |
| methanol (ppm) | ≤3000 ppm | ND |
| dimethylformamide (ppm) | ≤880 ppm | ND |
| diisopropylethylamine (ppm) | ≤200 ppm | ND |
| Individual unspecified impurities (% w/w) | ≤0.05% | 0.03% |
| Total unspecified impurities (% w/w) | ≤0.30% | N/A |
| Total impurities (% w/w) | ≤0.67% | N/A |
| Enantiomeric excess (% ee) | ≥97% | N/A |
| Isomer ratio | 1.3-1.9 | N/A |
| Endotoxin (as E. coli; EU/g) | ≤26 | Conform |
| Total aerobic microbial content (cfu/g) | ≤200 | Conform |
| Water content | ≤13.0% | 5.1% |

A number of embodiments of the invention have been described. Nevertheless, it will be understood that various modifications may be made without departing from the spirit and scope of the invention.

What is claimed is:

1. A process for preparing a pharmaceutically acceptable formulation of gadofosveset trisodium monohydrate, comprising:

(i) reacting (R)-2-amino-3-((2-aminoethyl)amino)propan-1-ol trihydrochloride with at least five equivalents of tert-butyl 2-bromoacetate to form a solution comprising a compound of Formula (1):

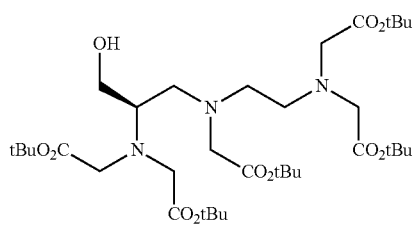

(ii) after (i), treating the solution with diethanolamine in an amount sufficient to consume any remaining tert-butyl 2-bromoacetate;

(iii) reacting 1,1'-(((4,4-diphenylcyclohexyl)oxy)phosphinediyl)bis(1H-imidazole) with the compound of Formula (1) to form a compound of Formula (2):

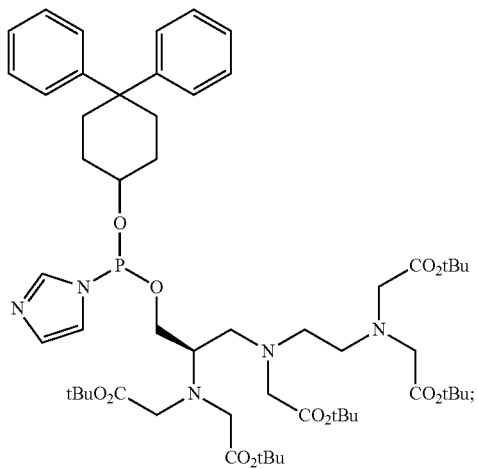

(iv) hydrolyzing and oxidizing the compound of formula (2) in the presence of hydrochloric acid and hydrogen peroxide to form a compound of Formula (3):

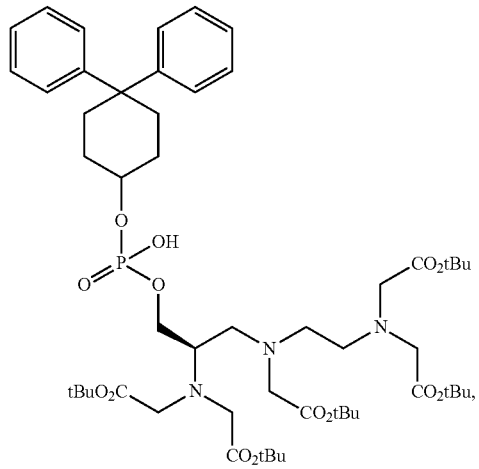

followed by further hydrolysis in the presence of hydrochloric acid to form fosveset; and (v) reacting an aqueous solution of said fosveset with gadolinium oxide, followed by reaction with sodium hydroxide to form gadofosveset trisodium monohydrate;

wherein said process comprises no more than one chromatographic purification for removal of impurities.

2. The process of claim 1, wherein, in (v), an excess of gadolinium oxide is reacted with the aqueous solution of the fosveset.

3. The process of claim 2, wherein, in (v), about 1.01 molar equivalents of gadolinium oxide is reacted with the aqueous solution of the fosveset.

4. The process of claim 1, further comprising, prior to (i):
(b) reacting dichloro((4,4-diphenylcyclohexyl)oxy)phosphine with 1H-imidazole to form the 1,1'-(((4,4-diphenylcyclohexyl)oxy)phosphinediyl)bis(1H-imidazole).

5. The process of claim 4, further comprising, prior to (b):
(a) reacting 4,4-diphenylcyclohexanol with phosphorous trichloride to form the dichloro((4,4-diphenylcyclohexyl)oxy)phosphine.

6. The process of claim 1, further comprising filtering an aqueous solution of gadofosveset trisodium monohydrate at a pH greater than 7.5.

7. The process of claim 6, wherein the solution is filtered at a pH of about 9 to about 12.

8. The process of claim 7, wherein the solution is filtered at a pH of about 10.5.

9. The process of claim 1, further comprising treating an aqueous solution of gadofosveset trisodium monohydrate with a strong acid cation exchange resin.

10. The process of claim 9, wherein the pH of the solution of gadofosveset trisodium monohydrate after said treating is adjusted to about 6 to about 7.

11. The process of claim 10, wherein the pH of the solution after said treating is adjusted to about 6.5.

12. The process of claim 9, wherein the resin comprises polystyrene crosslinked by divinylbenzene.

13. The process of claim 1, wherein the formulation comprises equal to or less than 0.6% w/w, 0.5% w/w, 0.4% w/w, 0.3% w/w, 0.2% w/w, 0.1% w/w, 0.09% w/w, 0.08% w/w, 0.07% w/w, 0.06% w/w, or 0.05% w/w total impurities based on gadofosveset trisodium.

14. The process of claim 1, further comprising, after (ii):
adding the solution of the compound of Formula (1) to a mixture of water and heptane, separating the organic phase, and extracting the organic phase with water to form an organic solution of the compound of Formula (1); and
filtering the organic solution through a column of silica gel.

15. The process of claim 1, comprising, prior to (i):
(i-a) reacting L-serine methyl ester hydrochloride with di-tert-butyl dicarbonate in the presence of triethylamine in a solvent comprising toluene to form N-(tert-butoxycarbonyl)-L-serine methylester;
(i-b) after (i-a), washing the solution with an aqueous brine solution;
(i-c) after (i-b), reacting the N-(tert-butoxycarbonyl)-L-serine methylester in toluene with 1,2-ethylenediamine to form a solution of (S)-tert-butyl (1-((2-aminoethyl)amino)-3-hydroxy-1-oxopropan-2-yl)carbamate in a solvent comprising toluene;
(i-d) after (i-c), concentrating the solution to form a solid, slurrying the solid, concentrating the slurry to form a solid, and crystallizing the solid from a solvent comprising tetrahydrofuran;
(i-e) after (i-d), reacting (S)-tert-butyl (1-((2-aminoethyl)amino)-3-hydroxy-1-oxopropan-2-yl)carbamate with diborane produced in situ to form (R)-tert-butyl (1-((2-aminoethyl)amino)-3-hydroxypropan-2-yl)carbamate; and
(i-f) after (i-e), reacting (R)-tert-butyl (1-((2-aminoethyl)amino)-3-hydroxypropan-2-yl)carbamate with hydrochloric acid in water to form (R)-2-amino-3-((2-aminoethyl)amino)propan-1-ol trihydrochloride.

16. The process of claim 5, comprising, prior to step (a), hydrogenating 4,4-diphenylcyclohex-2-enone in tetrahydrofuran in the presence of Raney nickel and hydrogen.

* * * * *